United States Patent
Tu (10) Patent No.: US 9,127,282 B2
(45) Date of Patent: Sep. 8, 2015

(54) FUSION PROTEINS OF BACTERIAL LUCIFERASE AS MULTICOLOR LUMINESCENT SENSORS

(75) Inventor: Shiao-Chun Tu, Houston, TX (US)

(73) Assignee: University of Houston System, Houston, TX (US)

( * ) Notice: Subject to any disclaimer, the term of this patent is extended or adjusted under 35 U.S.C. 154(b) by 322 days.

(21) Appl. No.: 13/531,558

(22) Filed: Jun. 24, 2012

(65) Prior Publication Data
US 2013/0023027 A1    Jan. 24, 2013

Related U.S. Application Data

(60) Provisional application No. 61/500,826, filed on Jun. 24, 2011.

(51) Int. Cl.
*C12N 9/96* (2006.01)
*C12N 15/62* (2006.01)

(52) U.S. Cl.
CPC ............ *C12N 15/62* (2013.01); *C07K 2319/60* (2013.01); *C07K 2319/61* (2013.01)

(58) Field of Classification Search
None
See application file for complete search history.

(56) References Cited

U.S. PATENT DOCUMENTS

| 5,976,796 A | 11/1999 | Szalay |
| 2004/0214227 A1 | 10/2004 | Joly |

FOREIGN PATENT DOCUMENTS

| EP | 1064360 B1 | 5/2008 |
| WO | 98/14605 A1 | 9/1998 |
| WO | 99/66324 A2 | 12/1999 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Close, D. M., S. S. Patterson, S. Ripp, S. J. Baek, J. Sanseverino and G. S. Sayler. Autonomous bioluminescent expression of the bacterial luciferase gene cassette (lux) in a mammalian cell line. Plos One 5, 2010, e12441.
Jawanda, N., K. Ahmed and S.-C. Tu. Vibrio harveyi flavin reductase-luciferase fusion protein mimics a single-component bifunctional monooxygenase. Biochemistry 47, 2008, 368-377.
Tu, S.-C. Bacterial bioluminescence: Biochemistry. In CRC Handbook of Organic Photochemistry and Photobiology 2nd Edition. (Edited by W. M. Horspool and F. Lenci). 2004, pp. 136.1-136.17, CRC Press, Boca Raton, FL.
Shaner, N. C., R. E. Campbell, P. A. Steinbach, B. N. G. Giepmans, A. E. Palmer and R. Y. Tsien. Improved monomeric red, orange and yellow fluorescent proteins derived from Discosoma sp red fluorescent protein. Nature Biotechnology 22, 2004, 1567-1572.
Lin, L. Y. C., R. Szittner, R. Friedman and E. A. Meighen. Changes in the kinetics and emission spectrum on mutation of the chromophore-binding platform in Vibrio harveyi luciferase. Biochemistry 43, 2004, 3183-3194.
Viviani, V., A. Uchida, N. Suenaga, M. Ryufuku and Y. Ohmiya. Thr226 is a key residue for bioluminescence spectra determination in beetle luciferases. Biochem. Biophys. Res. Commun. 280, 2001, 1286-1291.
Wang, H., B. F. Lei and S.-C. Tu. Vibrio harveyi NADPH-FMN oxidoreductase Arg203 as a critical residue for NADPH recognition and binding. Biochemistry 39, 2000, 7813-7819.
Choi, H., C. K. Tang and S.-C. Tu. Catalytically active forms of the individual subunits of Vibrio harveyi luciferase and their kinetic and binding properties. Journal of Biological Chemistry 270, 1995, 16813-16819.
Petushkov, V. N., B. G. Gibson and J. Lee. Properties of recombinant fluorescent proteins from Photobacterium leiognathi and their interaction with luciferase intermediates. Biochemistry 34, 1995, 3300-3309.
Karatani, H. And J. W. Hastings. Two active forms of the accessory yellow fluorescence protein of the luminous bacterium Vibrio fischeri strain Y1. J. Photochem. Photobiol. B: Biol. 18, 1993, 227-232.
Karatani, H., T. Wilson and J. W. Hastings. A blue fluorescent protein from a yellow-emitting luminous bacterium. Photochemistry and Photobiology 55, 1992, 293-299.
Meighen, E. A. Molecular biology of bacterial bioluminescence. Microbiol. Rev. 55,1991, 123-142.
Eckstein, J. W., K. W. Cho, P. Colepicolo, S. Ghisla, J. W. Hastings and T. Wilson. A time-dependent bacterial bioluminescence emission spectrum in an in vitro single turnover system. Energy transfer alone cannot account for the yellow emission of Vibrio fischeri Y-1. Proceedings of the National Academy of Sciences of the United States of America 87, 1990, 1466-1470.
Lee, J., D. J. Okane and B. G. Gibson. Bioluminescence spectral and fluorescence dynamics study of the interaction of lumazine protein with the intermediates of bacterial luciferase bioluminescence. Biochemistry 28, 1989, 4263-4271.
Hastings, J. W. C. J. Potrikus, S. C. Gupta, M. Kurfürst and J. C. Makemson. Biochemistry and physiology of bioluminescent bacteria. Adv. Microb. Physiol. 26, 1985, 235-291.
Hastings, J. W., T. O. Baldwin and M. Z. Nicoli. Bacterial luciferase: Assay, purification, and properties. Methods Enzymol. 57, 1978, 135-152.

(Continued)

*Primary Examiner* — Christian Fronda
(74) *Attorney, Agent, or Firm* — Jackson Walker L.L.P.

(57) ABSTRACT

The present invention discloses systems and methods for altering the color of bacterial bioluminescence via a fusion protein complex by fusing *Discosoma* sp. fluorescent protein mOrange (mOrange) with *Vibrio harveyi* luciferase. The fusion of mOrange to the N- or C-terminus of either α or β subunit of luciferase, via a short peptide linker produces fully active fusion enzymes. The fusion of mOrange to the N-terminus of luciferase α gives rise to a new 560-nm emission component. The same methodology may be used to alter bacterial bioluminescence color by covalent attachment of other suitable fluorescent proteins or chromophores to luciferase for generating multi-color sensors.

11 Claims, 6 Drawing Sheets

(56) References Cited

OTHER PUBLICATIONS

Cline, T. W. And J. W. Hastings. Mutated luciferases with altered bioluminescence emission spectra. J. Biol. Chem. 249, 1974, 4668-4669.

Meighen, E. A. and J. W. Hastings. Binding site determination from kinetic data. Reduced flavin moonucleotide binding to Bacterial luciferase. Journal of Biological Chemistry 246, 1971, 7666-7674.

Mitchell, G. and J. W. Hastings. The effect of flavin isomers and analogues upon the color of bacterial bioluminescence. J. Biol. Chem. 244, 1969, 2572-2576.

Hastings, J. W. and G. Weber. Total quantum flux of isotropic sources. Journal of the Optical Society of America 53, 1963, 1410-1415.

Ke, D. et al. Activities, kinetics and emission spectra of bacterial luciferase-fluorescent protein fusion enzymes. Journal of Photochemistry and Photobiology. Dec. 2011. vol. 87, No. 6, pp. 1346-1353.

Branchini, B. R. et al. Sequential bioluminescence resonance energy transfer-fluorescence resonance energy transfer-based ratiometric protease assays with fusion proteins of firefly luciferase and red fluorescent protein. Analytical Biochemistry. Jul. 15, 2011. vol. 414, No. 2, pp. 239-245. Epub Mar. 19, 2011.

De, A. et al. BRET3: a red-shifted bioluminescence resonance energy transfer (BRET)-based integrated platform for imaging protein-protein interactions from single live cells and living animals. FASEB Journal. Aug. 2009. vol. 23, No. 8, pp. 2702-2709.

Breton, B. et al. Multiplexing of multicolor bioluminescence resonance energy transfer. Biophysical Journal. Dec. 15, 2010, vol. 99, No. 12, pp. 4037-4046.

\* cited by examiner

| Luciferase | Bioluminescence activity ($\times 10^{22}$ q/mol/s) | Luciferase | Bioluminescence activity ($\times 10^{22}$ q/mol/s) |
| --- | --- | --- | --- |
| Wild-type α:β | 1.6 ± 0.1 | β:α-L$_5$-OFP | 1.4 ± 0.1 |
| OFP-L$_5$-α:β | 1.4 ± 0.1 | α:β-L$_5$-OFP | 1.4 ± 0.0 |
| OFP-L$_5$-β:α | 1.0 ± 0.1 | OFP-L$_{10}$-α:β | 1.4 ± 0.0 |

FIGURE 6

| Luciferase | $K_m$ (μM) | | Light decay rate (min$^{-1}$) | | |
| --- | --- | --- | --- | --- | --- |
| | decanal | FMNH$_2$ | whole light | 480 nm | 570 nm |
| Wild-type α:β | 1.13 ± 0.12 | 0.20 ± 0.02 | 5.8 ± 0.1 | 5.5 ± 0.2 | |
| OFP-L$_5$-α:β | 1.65 ± 0.14 | 0.18 ± 0.02 | 6.2 ± 0.1 | 6.1 ± 0.5 | 6.5 ± 0.1 |

SEQUENCE LISTING

```
<160> NUMBER OF SEQ ID NOS: 28

<210> SEQ ID NO 1
<211> LENGTH: 5
<212> TYPE: PRT
<213> ORGANISM: Artificial Sequence
<220> FEATURE:
<223> OTHER INFORMATION: 5-residue peptide linker

<400> SEQUENCE: 1

Gly Gly Gly Gly Thr
1               5

<210> SEQ ID NO 2
<211> LENGTH: 10
<212> TYPE: PRT
<213> ORGANISM: Artificial Sequence
<220> FEATURE:
<223> OTHER INFORMATION: 10-residue peptide linker

<400> SEQUENCE: 2
```

Gly Gly Gly Gly Thr Gly Gly Gly Gly Thr
1               5                   10

<210> SEQ ID NO 3
<211> LENGTH: 20
<212> TYPE: DNA
<213> ORGANISM: Artificial Sequence
<220> FEATURE:
<223> OTHER INFORMATION: forward primer 1 for mOrange amplification

<400> SEQUENCE: 3
ggaattccat atggtgagca                                           20

<210> SEQ ID NO 4
<211> LENGTH: 21
<212> TYPE: DNA
<213> ORGANISM: Artificial Sequence
<220> FEATURE:
<223> OTHER INFORMATION: reverse primer 1 for mOrange amplification

<400> SEQUENCE: 4
cgcggatcct acttgtacag c                                         21

<210> SEQ ID NO 5
<211> LENGTH: 20
<212> TYPE: DNA
<213> ORGANISM: Artificial Sequence
<220> FEATURE:
<223> OTHER INFORMATION: forward primer 1 for luxAB amplification

<400> SEQUENCE: 5
agcggatcca tgaaatttgg                                           20

<210> SEQ ID NO 6
<211> LENGTH: 23
<212> TYPE: DNA
<213> ORGANISM: Artificial Sequence
<220> FEATURE:
<223> OTHER INFORMATION: reverse primer 1 for luxAB amplification

<400> SEQUENCE: 6
cgtcaagctt acgagtggta ttt                                       23

<210> SEQ ID NO 7
<211> LENGTH: 15
<212> TYPE: DNA
<213> ORGANISM: Artificial Sequence
<220> FEATURE:
<223> OTHER INFORMATION: nucleotide sequence for L5

<400> SEQUENCE: 7
ggaggaggag gaaca                                                15

<210> SEQ ID NO 8
<211> LENGTH: 55
<212> TYPE: DNA
<213> ORGANISM: Artificial Sequence
<220> FEATURE:
<223> OTHER INFORMATION: forward primer for constructing pET28b-
      mOrange-L5-a:b

<400> SEQUENCE: 8
gcatggacga gctgtacaag ggaggaggag gaacaatgaa atttggaaac ttcct    55

<210> SEQ ID NO 9
<211> LENGTH: 55

<212> TYPE: DNA
<213> ORGANISM: Artificial Sequence
<220> FEATURE:
<223> OTHER INFORMATION: reverse primer for constructing pET28b-
      mOrange-L5-a:b

<400> SEQUENCE: 9
aggaagtttc caaatttcat tgttcctcct cctcccttgt acagctcgtc catgc      55

<210> SEQ ID NO 10
<211> LENGTH: 47
<212> TYPE: DNA
<213> ORGANISM: Artificial Sequence
<220> FEATURE:
<223> OTHER INFORMATION: forward primer for constructing pET28b-
      mOrange-L10-a:b

<400> SEQUENCE: 10
ggacgagctg tacaagggag gaggaggaac aggaggagga ggaacaa      47

<210> SEQ ID NO 11
<211> LENGTH: 47
<212> TYPE: DNA
<213> ORGANISM: Artificial Sequence
<220> FEATURE:
<223> OTHER INFORMATION: reverse primer for constructing pET28b-
      mOrange-L10-a:b

<400> SEQUENCE: 11
ttgttcctcc tcctcctgtt cctcctcctc ccttgtacag ctcgtcc      47

<210> SEQ ID NO 12
<211> LENGTH: 22
<212> TYPE: DNA
<213> ORGANISM: Artificial Sequence
<220> FEATURE:
<223> OTHER INFORMATION: forward primer 2 for luxAB amplification

<400> SEQUENCE: 12
cgtccatatg aaatttggaa ac      22

<210> SEQ ID NO 13
<211> LENGTH: 21
<212> TYPE: DNA
<213> ORGANISM: Artificial Sequence
<220> FEATURE:
<223> OTHER INFORMATION: forward primer 2 for mOrange amplification

<400> SEQUENCE: 13
cgtcaagctt atggtgagca a      21

<210> SEQ ID NO 14
<211> LENGTH: 19
<212> TYPE: DNA
<213> ORGANISM: Artificial Sequence
<220> FEATURE:
<223> OTHER INFORMATION: reverse primer 2 for mOrange amplification

<400> SEQUENCE: 14
tacggccgac ttgtacagc      19

<210> SEQ ID NO 15
<211> LENGTH: 47
<212> TYPE: DNA
<213> ORGANISM: Artificial Sequence
<220> FEATURE:
<223> OTHER INFORMATION: forward primer for constructing pET21b-a:b-L5- mOrange

<400> SEQUENCE: 15
cgtcaaatac cactcgggag gaggaggaac aatggtgagc aagggcg          47

<210> SEQ ID NO 16
<211> LENGTH: 47
<212> TYPE: DNA
<213> ORGANISM: Artificial Sequence
<220> FEATURE:
<223> OTHER INFORMATION: reverse primer for constructing pET21b-a:b-L5-
      mOrange

<400> SEQUENCE: 16
cgcccttgct caccattgtt cctcctcctc ccgagtggta tttgacg          47

<210> SEQ ID NO 17
<211> LENGTH: 27
<212> TYPE: DNA
<213> ORGANISM: Artificial Sequence
<220> FEATURE:
<223> OTHER INFORMATION: forward primer for luxB amplification

<400> SEQUENCE: 17
gaccatatga aatttggatt attcttc                               27

<210> SEQ ID NO 18
<211> LENGTH: 24
<212> TYPE: DNA
<213> ORGANISM: Artificial Sequence
<220> FEATURE:
<223> OTHER INFORMATION: reverse primer for luxB amplification

<400> SEQUENCE: 18
gatggatcct tacgagtggt attt                                  24

<210> SEQ ID NO 19
<211> LENGTH: 23
<212> TYPE: DNA
<213> ORGANISM: Artificial Sequence
<220> FEATURE:
<223> OTHER INFORMATION: forward primer for luxA amplification

<400> SEQUENCE: 19
cagagctcat gaaatttgga aac                                   23

<210> SEQ ID NO 20
<211> LENGTH: 25
<212> TYPE: DNA
<213> ORGANISM: Artificial Sequence
<220> FEATURE:
<223> OTHER INFORMATION: reverse primer for luxA or luxBA amplification

<400> SEQUENCE: 20
cgtcaagctt actgttttc tttga                                  25

<210> SEQ ID NO 21
<211> LENGTH: 60
<212> TYPE: DNA
<213> ORGANISM: Artificial Sequence
<220> FEATURE:
<223> OTHER INFORMATION: forward primer for constructing pET21b-b:a

<400> SEQUENCE: 21
aacatcgtca ataccactcg gtaaaaggag agagacatga aatttggaaa cttccttctc    60

<210> SEQ ID NO 22
<211> LENGTH: 60
<212> TYPE: DNA
<213> ORGANISM: Artificial Sequence
<220> FEATURE:
<223> OTHER INFORMATION: reverse primer for constructing pET21b-b:a

<400> SEQUENCE: 22
gagaaggaag tttccaaatt tcatgtctct ctccttttac gagtggtatt tgacgatgtt    60

<210> SEQ ID NO 23
<211> LENGTH: 53
<212> TYPE: DNA
<213> ORGANISM: Artificial Sequence
<220> FEATURE:
<223> OTHER INFORMATION: forward primer for constructing pET21b-b:a-L5-
      mOrange

<400> SEQUENCE: 23
atatctcaaa gaaaaacagg gaggaggagg aacaatggtg agcaagggcg agg    53

<210> SEQ ID NO 24
<211> LENGTH: 53
<212> TYPE: DNA
<213> ORGANISM: Artificial Sequence
<220> FEATURE:
<223> OTHER INFORMATION: reverse primer for constructing pET21b-b:a-L5-
      mOrange

<400> SEQUENCE: 24
cctcgccctt gctcaccatt gttcctcctc ctccctgttt tctttgaga tat    53

<210> SEQ ID NO 25
<211> LENGTH: 23
<212> TYPE: DNA
<213> ORGANISM: Artificial Sequence
<220> FEATURE:
<223> OTHER INFORMATION: forward primer for luxBA amplification

<400> SEQUENCE: 25
tacggatcca tgaaatttgg att    23

<210> SEQ ID NO 26
<211> LENGTH: 58
<212> TYPE: DNA
<213> ORGANISM: Artificial Sequence
<220> FEATURE:
<223> OTHER INFORMATION: forward primer for constructing pET28b-
      mOrange-L5-b:a

<400> SEQUENCE: 26
ggcatggacg agctgtacaa gggaggagga ggaacaatga aatttggatt attcttcc    58

<210> SEQ ID NO 27
<211> LENGTH: 58
<212> TYPE: DNA
<213> ORGANISM: Artificial Sequence
<220> FEATURE:
<223> OTHER INFORMATION: reverse primer for constructing pET28b-
      mOrange-L5-b:a

<400> SEQUENCE: 27
ggaagaataa tccaaatttc attgttcctc ctccctt gtacagctcg tccatgcc    58

<210> SEQ ID NO 28
<211> LENGTH: 20

-continued

```
<212> TYPE: PRT
<213> ORGANISM: Artificial Sequence
<220> FEATURE:
<223> OTHER INFORMATION: 20-residue peptide

<400> SEQUENCE: 28

Met Gly Ser Ser His His His His His His Ser Ser Gly Leu Val Pro
1               5                   10                  15

Arg Gly Ser His
            20
```

US 9,127,282 B2

FUSION PROTEINS OF BACTERIAL LUCIFERASE AS MULTICOLOR LUMINESCENT SENSORS

TECHNICAL FIELD

This disclosure relates in general to the field of luminescent sensors and more particularly to fusion proteins of luciferase as luminescent sensors.

SEQUENCE LISTING

The instant application contains a Sequence Listing which has been submitted in ASCII format via EFS-Web and is hereby incorporated by reference in its entirety. Said ASCII copy, created on Sep. 27, 2012, is named HOUS004US0_v1_ST25.txt and is 6,451 bytes in size.

BACKGROUND

Multiple color emissions from a single bioluminescence system have often been the focus for extensive studies either for elucidation of luciferase or fluorescent protein structure-function relationships. Additionally, they have been studied for the development of improved sensors.

Bioluminescence derived from luciferase-catalyzed reactions and fluorescent protein emissions has been widely used in life sciences for both basic and applied studies. For most luciferases, the required luciferins that undergo luciferase-catalyzed oxidation are unusual metabolites specialized for bioluminescence reactions. If used for signaling or imaging purposes, it may be difficult or inconvenient to provide these unusual luciferins to the systems under investigation, especially for in vivo studies.

In this way, bacterial luciferase-catalyzed bioluminescence has some unique advantages over other luciferase systems. Oxygen and reduced riboflavin 5'-phosphate ($FMNH_2$), e.g., two of the three substrates required by bacterial luciferase for producing luminescence, are readily available in various cell types. The third substrate for the bacterial luciferase-catalyzed oxidative process, long-chain aliphatic aldehyde, cannot be generated by most other cell types. However, the long-chain aldehydes may be synthesized by the luxCDE genes in luminous bacteria. Further, these long-chain aldehydes have very high binding affinities for luciferase, with $K_m$ below micromolar levels, and due to their highly hydrophobic nature, can easily diffuse through cell membranes for in vivo imaging applications.

The aldehyde-generating genes may be cloned along with luxAB genes for bacterial luciferase α and β subunits into the cell systems. Moreover, the codon-optimized *Vibrio harveyi* luciferase lux genes and the frp gene for flavin reductase P (FRP), which generates $FMNH_2$ from FMN using NADPH as a reductant, have been successfully expressed in mammalian HEK 293 cells with significant signals for bioluminescence imaging. The lux genes have been well characterized, and the structures and reaction mechanisms of bacterial luciferase have also been extensively studied, making bacterial luciferase particularly suitable for serving as a reporting system.

However, as applied for current in vivo systems, the normal 490 nm emission by bacterial luciferase suffers from two disadvantages, namely absorption by some cellular components and a lower ability to penetrate tissue.

In this connection, changes in the color of bacterial luciferase bioluminescence have previously been reported in three lines of studies. First, replacements of the $FMNH_2$ substrate by reduced 2-thioFMN and iso-FMN were found to shift the 490 nm peak of the bioluminescence to 530 and 470 nm, respectively. Second, certain mutations of the bacterial luciferase active center structure also led to changes of the bioluminescence color. In another study, the luciferase α subunit was randomly mutated and five luciferase variants were found to emit bioluminescence with significant but limited shifts from that of the normal 490 nm emission. This finding suggested that the excited emitter is bound to luciferase and its emission is sensitive to the environment of the luciferase active site. The luciferase α subunit was also subjected to controlled single- to triple-residue mutations for altering the emission spectrum. Third, bacterial bioluminescence color, in vitro and in vivo, may also be changed by the formation of a non-covalent complex of luciferase with specific fluorescent proteins co-existing in luminous bacteria. These fluorescent proteins include a lumazine protein from *Photobacterium phosphoreum* and *Photobactreum leiognothi*, two forms of yellow-fluorescent proteins, and a blue-fluorescent protein from *Vibrio fischeri* strain Y1.

Some have used certain flavin analogs for altering the bacterial luciferase emission color in vitro, however, it is not applicable to in vivo systems. Additionally, due to the rather stringent specificity of luciferase for the flavin substrate, color changes of bacterial luciferase bioluminescence by flavin analogs other than 2-thioFMN and iso-FMN have not been reported. Others have changed the luciferase active site structure as a way to alter bacterial luminescence color by either random mutation or site-directed mutagenesis, and producing luciferase variants that generally have substantially reduced activities and their emission spectral changes are limited (up to 12 nm shifts to the red).

Others have blue-shifted, by about 10- and 20-nm peak, the normal 490-nm bioluminescence of luciferase by the blue fluorescent protein and lumazine protein, respectively, and red shifted to near 540 nm by the yellow fluorescent proteins. Lumazine protein and yellow fluorescent protein each interacts specifically and directly with luciferase reaction intermediate(s) to alter not only the color but also the reaction kinetics of the luciferase-catalyzed emission. This may be best demonstrated by the single turnover reaction by luciferase in the presence of yellow fluorescent protein, in which the decay rates of the 490 nm normal bioluminescence by luciferase and the 540 nm emission from yellow fluorescent protein were distinct. Therefore, the emission spectrum actually changes over time and resonance energy transfer alone cannot account for the change of emission color.

Prior studies have reported that lumazine protein, blue and yellow fluorescent proteins do not have the ability to alter the bioluminescence spectra of all known bacterial luciferases; one species of fluorescent protein can change the bioluminescence color of only one or a very limited few species of luciferase. Moreover, it has been reported that their non-covalent interactions with corresponding luciferases are sensitive to perturbations by factors such as temperature and concentration.

Although various compositions and methods for altering the color of luciferase luminescence are known to the art, all, or almost all of them suffer from one or more than one disadvantage and have shortcomings. Therefore a need has arisen for compositions and methods for changing the color of luciferase bioluminescence which corrects the problems identified above, and enables its use in vivo or as part of multi-color sensor systems.

SUMMARY

The following disclosure presents concepts for regulation of the emission spectrum of bacterial luciferase. The disclosed subject matter significantly improves upon prior art aimed at altering the color of bioluminescence derived from luciferase-catalyzed reactions.

It is an object of the present disclosure to permit compositions that are well suited for biological applications including in vitro and in vivo sensing, and enhancement of tissue imaging. Another object of the present disclosure is to permit various aspects and embodiments of a luminescent sensor system and its associated methods of use and methods of manufacture.

In preferred embodiments, the compositions exhibit luciferases from desired luminous bacteria or engineered luciferases as the energy donor, and desired species of fluorescent proteins as the energy acceptor.

One aspect of the disclosed subject matter is that energy donors may generally encompass native or engineered luciferases including, but not limited to: alpha-beta non-fused or fused luciferase or any bacterial luciferase genes which have been modified for expression in eukaryotic cells.

In another aspect of preferred embodiments, energy acceptors may include any appropriate fluorescent proteins provided that their absorption spectra overlap somehow with the emission of normal bioluminescence, and that their fluorescence emission spectra are in a wavelength range higher than the normal luciferase bioluminescence.

In other preferred embodiments, fusion of bacterial luciferase with a GFP-type fluorescent protein takes advantage of the proximity between these two partners of the fusion protein to allow the alteration of the luciferase's original 490-nm emission through bioluminescence resonance energy transfer (BRET) to the fluorescent protein.

These and other aspects of the disclosed subject matter, as well as additional novel features, will be more apparent from the following detailed description of preferred embodiments of the invention, along with the accompanying drawings in which like numerals represent like components. The intent of this summary is not to be a comprehensive description of the claimed subject matter, but rather to provide a short overview of some of the subject matter's functionality. Other systems, methods, objects, features, aspects, and advantages here provided will become apparent to one with skill in the art upon examination of the following FIGUREs and detailed description. It is intended that all such additional systems, methods, features and advantages that are included within this description, be within the scope of any claims filed later.

BRIEF DESCRIPTIONS OF THE DRAWINGS

The novel features believed characteristic of the presently disclosed subject matter will be set forth in any claims that are filed later. The presently disclosed subject matter itself, however, as well as a preferred mode of use, further objectives, and advantages thereof, will best be understood by reference to the following detailed description of an illustrative embodiment when read in conjunction with the accompanying drawings, wherein:

DETAILED DESCRIPTION OF THE SPECIFIC EMBODIMENTS

Although described with particular reference to compositions of fusion proteins and methods for the regulation of the emission spectrum of bacterial luciferases, those with skill in the arts will recognize that the disclosed embodiments have relevance to a wide variety of areas in addition to those specific examples described below.

All references, including publications, patent applications, and patents, cited herein are hereby incorporated by reference to the same extent as if each reference were individually and specifically indicated to be incorporated by reference and were set forth in its entirety herein.

Figure 1:
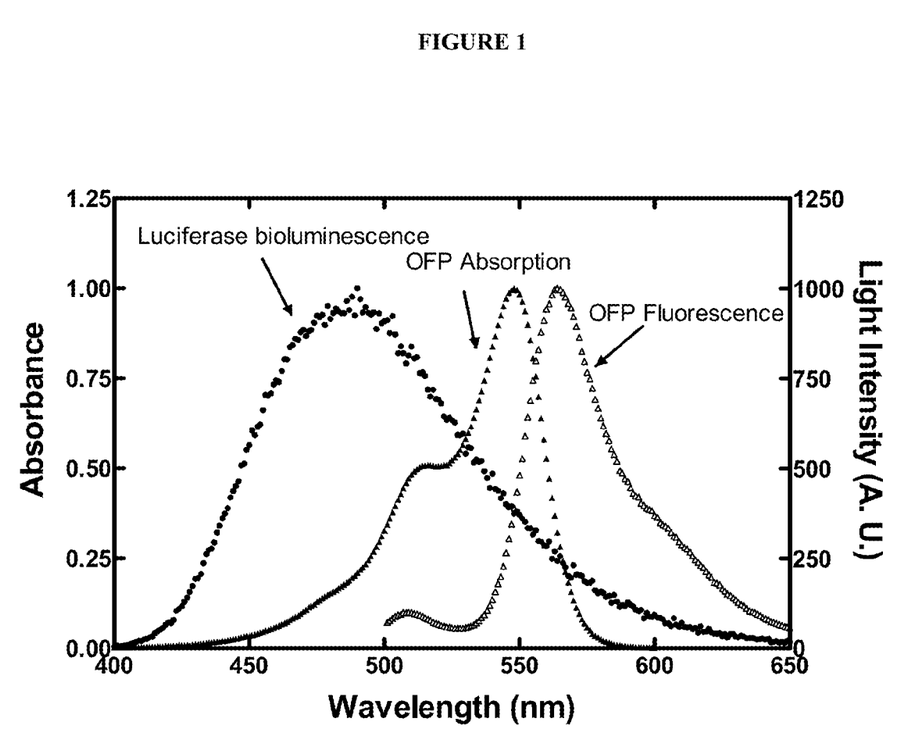
FIG. 1 is a graph of exemplary spectra of luciferase bioluminescence, mOrange absorption, and mOrange fluorescence as taught by the present disclosure.

FIG. 1 is a graph of exemplary spectra of luciferase bioluminescence, mOrange absorption, and mOrange fluorescence as taught by the present disclosure.

The present disclosure relates to methods for the regulation of the emission spectrum of bacterial luciferase. Additional embodiments of the present disclosure relate to the compositions of fusion enzymes, methods for making the same, and methods for their use. The compositions exhibit luciferases from desired luminous bacteria or engineered luciferases as the energy donor, and desired species of fluorescent proteins as the energy acceptor. Energy donors may generally encompass native or engineered luciferases including, but is not limited to: alpha-beta non-fused or fused luciferase or any bacterial luciferase genes which have been modified for expression in eukaryotic cells. Energy acceptors include any appropriate fluorescent proteins with the requirement that their absorption spectra overlap with the emission of normal bioluminescence, and that their fluorescence emission spectra are in a wavelength range higher than the normal luciferase bioluminescence. The benefit of such a composition is that it alters the color of bioluminescence derived from luciferase-catalyzed reactions. Embodiments of these compositions are well suited for biological applications including in vitro and in vivo sensing, and enhancement of tissue imaging.

A variety of fluorescent proteins related to the jellyfish *Aequorea* green fluorescent protein (GFP) have been developed to exhibit a wide range of fluorescence colors. An exemplary embodiment of the present disclosure includes a series of fusion proteins by linking *Vibrio harveyi* luciferase to *Discosoma* sp. fluorescent protein mOrange. The normal bioluminescence spectrum of native bacterial luciferase significantly overlaps with the absorption of mOrange, and the fluorescence emission peak of mOrange is at a longer wavelength than the peak of the luciferase bioluminescence. These properties indicate that mOrange may be an appropriate energy acceptor for the energy donor bacterial luciferase. The absorption and fluorescence emission spectra of 13 μM mOrange in the standard buffer (50 mM phosphate, pH 7.0) may be determined using an excitation light at 480 nm for the latter measurement. The luciferase bioluminescence emission spectrum was measured by the luciferase-FRP coupled assay in 1 mL standard buffer containing 0.5 mM dithiothreitol (DTT), 5.4 µM FRP, 2 mM NADPH, 100 µM decanal, 36 µM FMN, and 0.5 µM luciferase. All spectra may be measured at 23° C.

Although mOrange may be fused to any species of bacterial luciferase of choice, for exemplary purposes, the present disclosure describes how mOrange interacts with the bacterial luciferase, Vibrio harveyi luciferase. In one example, V. harveyi NADPH-specific flavin reductase FRP is used to continuously generate the required $FMNH_2$ substrate, and the resulting emission spectra produced by such fusion enzymes is disclosed. Expansion of this approach includes, for exemplary purposes, the substitution of mOrange with any desired fluorescent proteins, or by tagging luciferase with a suitable fluorescent acceptor chromophore.

Another exemplary embodiment of the present invention discloses the bioluminescence profiles and kinetic properties of fusion enzymes made of wild type luciferase, such as Vibrio harveyi luciferase, and Discosoma sp. fluorescent protein mOrange. These fusion proteins retain wild-type like bioluminescence activities. To achieve this, the following plasmids encoding the following fusion enzymes are constructed: mOrange-$L_5$-α:β, mOrange-$L_5$-β:α, β:α-$L_5$-mOrange, α:β-$L_5$-mOrange, and mOrange-$L_{10}$-α:β.

mOrange is fused to the N- or C-terminus of either the α or β subunit of bacterial luciferase through a GlyGlyGlyGlyThr (Seq. ID. No. 1: 5-residue peptide linker abbreviated $L_5$) five-residue (abbreviated $L_5$) or, in one case, a GlyGlyGlyGlyThrGlyGlyGlyGlyThr (Seq. ID. No. 2: 10-residue peptide linker abbreviated $L_{10}$) 10-residue linker to generate five fusion enzymes. After expression and purification, these fusion enzymes are obtained at 90% or greater purities and the expected molecular weights for luciferase α or β fused with mOrange are confirmed by patterns of SDS gel electrophoresis. Due to the tight binding between the two subunits of luciferase, the fusion enzymes are each isolated as a single complex of non-modified subunit and the mOrange-fused counter subunit.

The present disclosure teaches exemplary embodiments capable of generating emissions at wavelengths longer than 490 nm, such as the 560 nm emission by mOrange fused to luciferase. Both mOrange-$L_5$-α:β and mOrange-$L_{10}$-α:β fusion enzymes as described herein retain activities similar to that of the wild-type luciferase, and both show a substantial emission component at 560 nm, a 70 nm red shift from the known bacterial bioluminescence. These emissions at longer wavelengths suffer from much less absorption and have better efficiencies in penetrating tissues.

The new 560-nm component in the bioluminescence catalyzed by mOrange-$L_5$-α:β and mOrange-$L_{10}$-α:β as described herein is a direct consequence of bioluminescence resonance energy transfer (BRET). The fusion of a luciferase with a fluorescent protein of choice, and the related bioluminescence resonance energy transfer properties, results in a new emission component from such protein or any other appropriate acceptor. This offers a significant advantage in that no excitation light is required. Existing imaging systems often require an excitation light for the fluorescence of proteins, and have undesirable effects of generating unwanted background fluorescence and/or photo-bleaching of the fluorescent molecules. By contrast, the present disclosure does not require an excitation light and it is therefore a significant improvement over existing systems.

Rather, exemplary methods disclosed herein take advantage of BRET mechanics, wherein the energy of emission from the luciferase-fluorescent protein fusion is derived from the luciferase-catalyzed reaction. Since luciferase is a catalytic enzyme, even a trace amount of the fusion enzyme can magnify the output of light by the multiple turnovers of luciferase. In contrast, fluorescent proteins are not enzymes and, hence, cannot magnify light output by catalytic turnovers. Any low levels of fluorescent proteins can only produce low levels of fluorescence signals, which would be highly distorted by any excitation lights used to generate emissions from the fluorescent proteins alone.

By using covalent linkages between a luciferase and a fluorescent protein to vary the bioluminescent spectrum of fusion enzymes, the presence of the mOrange acceptor within proximity of the luciferase donor assures that energy transfer occurs. In addition to mOrange, a variety of GFP-related variants for a wide range of fluorescence emissions may be used. Therefore an extension of the present disclosure consists in using the methods for mOrange described herein to alter the bacterial luciferase bioluminescence spectrum by fusing luciferase with either other fluorescent proteins (GFP-related or not), or by chemically attachment of suitable fluorescent acceptor chromophores to luciferase.

Figure 2:
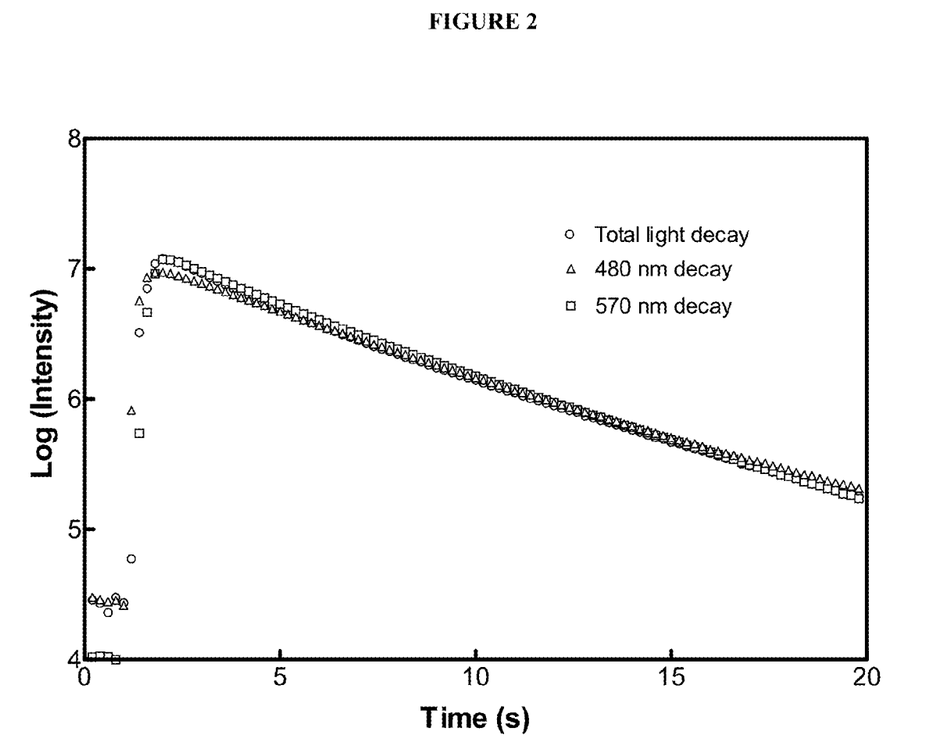
FIG. 2 displays a graph of the time courses of bioluminescence catalyzed by exemplary embodiments in a single turnover reaction.

FIG. 2 displays a graph of the time courses of bioluminescence catalyzed by exemplary embodiments in a single turnover reaction, or more specifically, the decay of bioluminescence catalyzed by mOrange-$L_5$-α:β in a single turnover reaction. Light emissions from mOrange-$L_5$-αβ in the dithionite assay may be monitored as either the total light, or intensities at 480 nm and 570 nm. The intensities may be normalized for comparison of the decay kinetics.

Figure 3:
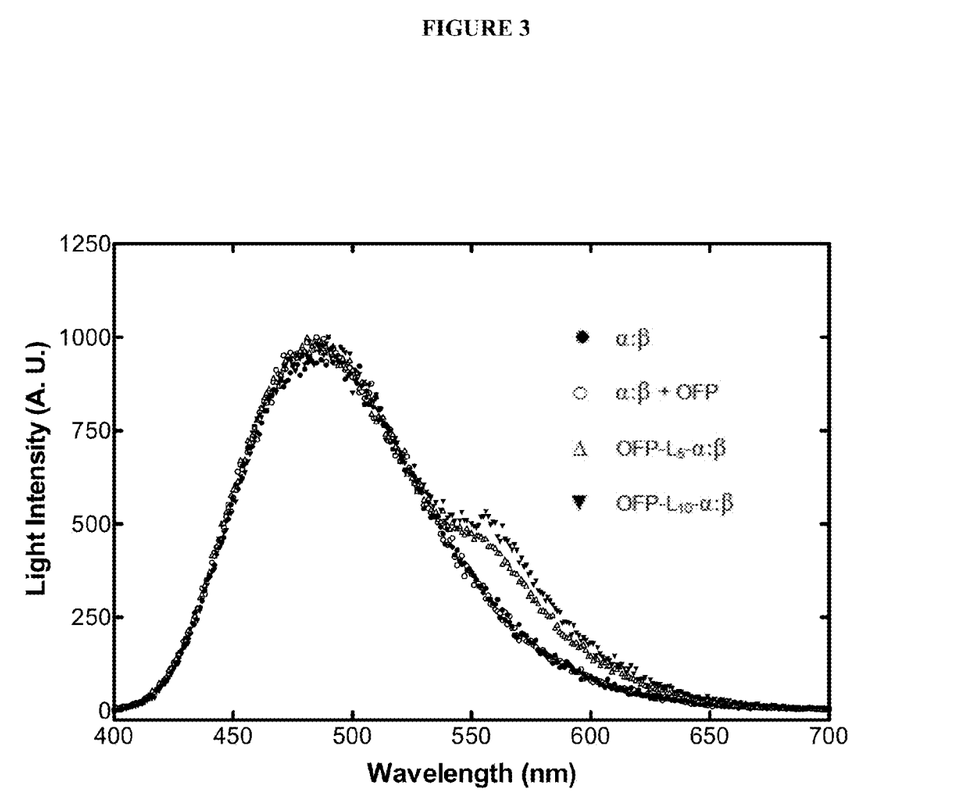
FIG. 3 displays a graph of bioluminescence spectra of the reactions catalyzed by various exemplary embodiments of the present disclosure.

FIG. 3 displays a graph of bioluminescence spectra of the reactions catalyzed by various exemplary embodiments of the present disclosure, or more specifically, the spectra of the reactions catalyzed by the wild-type luciferase (α:β), mOrange-$L_5$-α:β, and mOrange-$L_{10}$-α:β. The bioluminescence emission spectra may be measured by using the FRP-luciferase coupled assay at 23° C. in the standard buffer containing 0.5 mM DTT, 5.4 µM FRP, 2 mM NADPH, 100 µM decanal, and 36-70 µM FMN. Luciferase is also included at 0.5-1.2 µM as the wild-type enzyme, mOrange-$L_5$-α:β, or mOrange-$L_{10}$-α:β. As a control, another reaction may be carried out under identical condition except that the solution contained a mixture of free luciferase and mOrange, each at 0.5 µM. The emission intensities may be normalized to near the same level at 490 nm for spectral comparisons.

Figure 4:
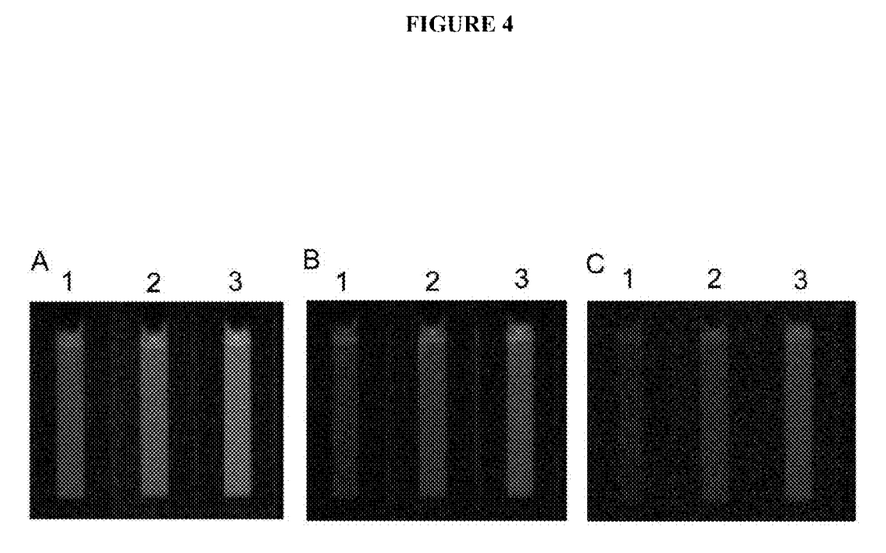
FIG. 4 depicts photographic images of the bioluminescence catalyzed by various exemplary embodiments of the present disclosure.

FIG. 4 depicts photographic images of the bioluminescence catalyzed by various exemplary embodiments of the present disclosure, which include bioluminescence catalyzed by the wild-type luciferase, mOrange-$L_5$-α:β, and mOrange-$L_{10}$-α:β. The FRP-luciferase coupled reactions may be carried out in fluorescent cuvettes identically as that described above except FMN may be at 69 µM and mOrange-$L_{10}$-α:β may be at 1 µM (Sample 3). The levels of wild-type luciferase (Sample 1) and mOrange-$L_5$-α:β (Sample 2) may be similar to that of mOrange-$L_{10}$-α:β but slightly adjusted to emit about the same intensity of light as that by mOrange-$L_{10}$-α:β. Photographs of these three samples may be taken in a dark room without filter (Panel A), or with a yellow filter (<1% transmission at <460 nm) (Panel B) or an amber filter (<1% transmission at <532 nm) (Panel C).

The differences in color of the bioluminescence emissions by the wild-type luciferase, mOrange-$L_5$-α:β and mOrange-$L_{10}$-α:β are evident by vision or direct photography. Panel A shows the bioluminescence from the three luciferase samples mentioned above, respectively, as images 1, 2, and 3. As such, the differences in color are not that apparent. However, when the sample is observed through a yellow cut-off filter (<1% transmission at <460 nm), the emission from the wild-type luciferase is mostly filtered out while the longer-wavelength emissions are clearly viewed for the mOrange-$L_5$-α:β and, more so, mOrange-$L_{10}$-α:β (Panel B). An even more pronounced difference in the emissions is observed when an amber cut-off filter (<1% transmission at <532 nm) is used (Panel C). In this case, the wild-type luciferase emission is almost entirely filtered out. Significant changes in luciferase bioluminescence color only occur when mOrange is fused to the N-terminus of the α subunit (e.g., mOrange-$L_5$-α:β and mOrange-$L_{10}$-α:β). No change of bioluminescence spectrum is observed when mOrange is attached to the N- or C-terminus of β or the C-terminus of α. The bioluminescent color varies depending upon (1) where on the luciferase the mOrange is attached to, and (2) the length of the residue linker.

Figure 5:
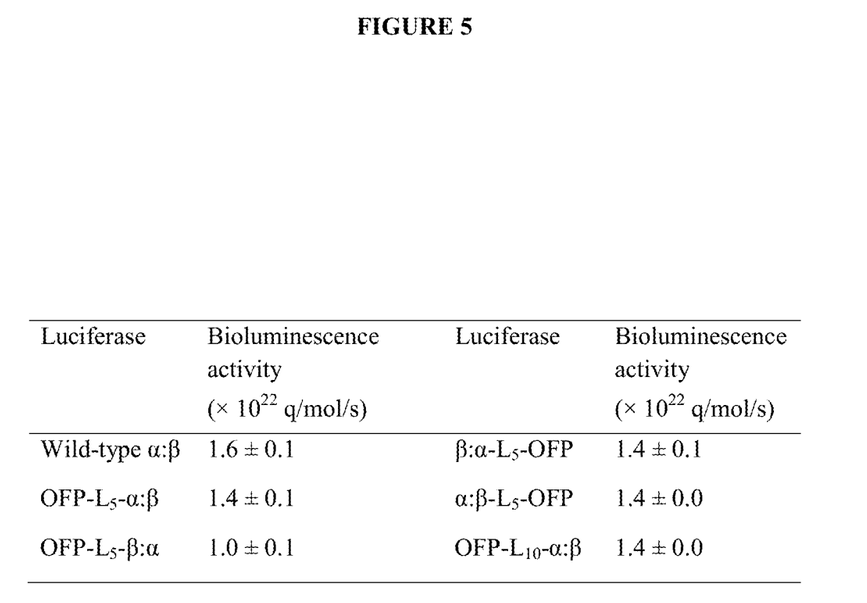
FIG. 5 illustrates a table of bioluminescence activities of exemplary embodiments of the present disclosure and those of wild-type luciferases.
Figure 6:
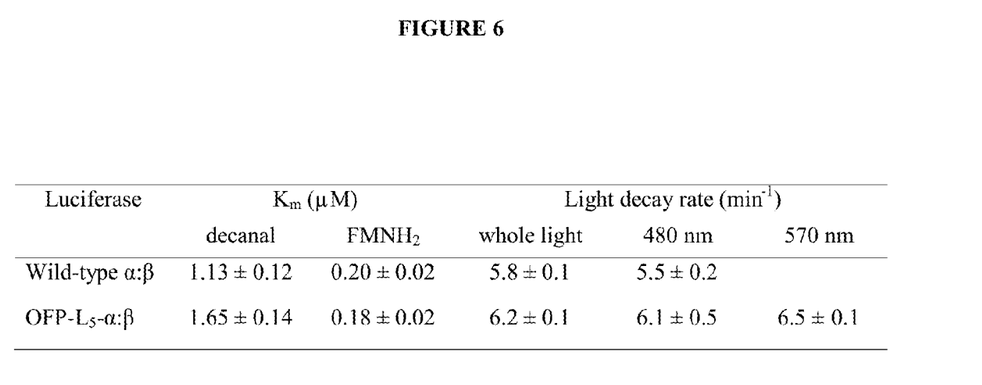
FIG. 6 illustrates a table of kinetic properties of exemplary embodiments of the present disclosure and those of wild-type luciferases.

FIG. 5 illustrates a table of bioluminescence activities of exemplary embodiments of the present disclosure and those of wild-type luciferases. Bioluminescence activities (peak intensities) of wild-type luciferase and luciferase-fluorescent protein fusion enzymes are shown for the activities of these fusion enzymes when examined using the dithionite assay. A general pattern emerges for all fusion enzymes: No significant change is observed in their bioluminescence activities in comparison with that of the wild-type luciferase, regardless whether mOrange is fused to the N- or C-terminus of either the luciferase α or β subunit. This is also the case for fusion enzyme mOrange-$L_5$-α:β where the change of the linker from 5 to 10 amino acid residues leads to no change in the fusion enzyme activity. The kinetic properties of mOrange-$L_5$-α:β closely resembles that of the wild-type luciferase with respect to $K_m$ values for decanal and $FMNH_2$, as shown the table of kinetic properties.

FIG. 6 illustrates a table of kinetic properties of exemplary embodiments of the present disclosure and those of wild-type luciferases. The time course of the bioluminescence decay of the wild-type luciferase in the non-turnover dithionite assay closely resembles that of a first-order process, with about the same decay rate when monitored as the total light or intensity at 480 nm. Similar results are also observed for mOrange-$L_5$-α:β when the bioluminescence emission is monitored as the total light, 480-nm intensity, or 570-nm intensity, except that the day rates are slightly faster relative to the wild-type luciferase. Additionally, when the intensities at the 490 nm peak are normalized to the same level, both mOrange-$L_5$-α:β and mOrange-$L_{10}$-α:β exhibit in their bioluminescence spectra an additional longer-wavelength emission shoulder near 560 nm, with a higher intensity for the latter. However, when luciferase is mixed with free mOrange, no 560-nm emission component is observed. These results clearly demonstrated that the 560-nm emissions from mOrange-$L_5$-α:β and mOrange-$L_{10}$-α:β are due to Bioluminescence Resonance Energy Transfer (BRET) from luciferase to the fused mOrange, as previously discussed. In contrast, the emission spectra of mOrange-$L_5$-α:β, β:α-$L_5$-mOrange and α:β-$L_5$-mOrange are identical to that of the wild-type luciferase.

The following disclosure teaches exemplary materials and general molecular biological methods for practicing the above disclosed inventions.

Decanal, riboflavin 5'-phosphate (FMN), dihydronicotinamide adenine dinucleotide phosphate (NADPH), dithiothreitol (DTT), kanamycin, ampicillin, isopropyl β-D-1-thiogalactopyranoside (IPTG), albumin from chicken egg white, sodium hydrosulfite and oligonucleotide primers may be purchased from various vendors. The vector mOrange carrying the mOrange-encoding mOrange gene may be purchased from various vendors. *Escherichia coli* BL21(DE3) and BL21(DE3)pLysS competent cells and the pET28b plasmid may be purchased from various vendors. The *E. coli* strain JM109 carrying the pUC19 plasmid (which contained the *V. harveyi* luciferase luxAB genes) and the *E. coli* strain BL21 carrying the pET21d plasmid (in which the frp gene encoding the NADPH-preferring flavin reductase FRP may be inserted between the NcoI and BamHI cutting sites) may be prepared as described previously. Restriction enzymes, T4 DNA ligase, Quick ligation kit and Phusion high-fidelity PCR kit may be purchased from various vendors. The QuikChange II site-directed mutagenesis kit and QuikChange lightning site-directed mutagenesis kit may be purchased from various vendors. QIAprep spin miniprep kit, QIA quick PCR purification kit and QIAquick gel extraction kit may be purchased from various vendors. Wizard SV gel and PCR clean-up system may be purchased from Promega. The DC Protein Assay Kit may be purchased from various vendors. The HisTrap HP column, HiPrep 26/10 desalting column, Hi-trap DEAF Sepharose column and Mono Q 5/50 GL column may be purchased from various vendors. Unless stated otherwise, a standard buffer of 50 mM phospate, pH 7.0, may be used.

A PTC-200 thermal cycler may be used for polymerase chain reaction (PCR). PCR amplification products may be purified by agarose gel (0.75%) electrophoresis and extracted by using either the QIA quick gel extraction kit or the Wizard SV gel and PCR clean-up system. After restriction enzyme digestions, DNA fragments may be purified by using a QIA quick PCR purification kit or a Wizard SV gel and PCR clean-up system. Desired DNA fragments may be ligated by using a Quick ligation kit or T4 ligase. Cell transformations may be carried out by following the protocol provided, and cells may be subsequently plated on LB agar plates containing 50 mg/L kanamycin or ampicillin with or without IPTG (100 µL 10 mM IPTG water solution may be spread on the agar surface of each plate 1 h before use). After overnight growth at 37° C., several colonies may be picked. Each colony may be cultured at 37° C. in a 15-mL tube containing 10 mL LB and 50 mg/L kanamycin or ampicillin with shaking at 250 revolutions per minute (rpm) for 12 h. Cells may be harvested and a QIAprep spin miniprep kit used to extract plasmids. After isolation, the desired plasmids may be all confirmed by sequencing.

Vectors pET28b-mOrange and pET28b-mOrange:α:β.

The mOrange gene may be amplified by PCR using the pmOrange plasmid and primers 5'-GGAATTC<u>CATATG</u>GTGAGCA-3'(Seq. ID. No. 3: forward primer 1 for mOrange amplification) and 5'-CGC<u>GGATCC</u>TACTTGTACAGC-3' (Seq. ID. No. 4: reverse primer 1 for mOrange amplification). The underlined sequences are recognized by the restriction enzymes NdeI and BamHI, respectively. The PCR amplification product may be purified and extracted. The purified sample so obtained and the pET28b plasmid may be double-digested by NdeI and BamHI, purified, and ligated. The ligation mixture may then be added to *E. coli* BL21(DE3) competent cells for transformation. Cells may then be plated on LB agar plates containing kanamycin and IPTG. Colony selection (by pink color), cell growth (in LB medium containing kanamycin), and plasmid extraction may be carried out as described above to obtain the pET28b-mOrange vector.

The luciferase luxAB genes may be amplified by PCR using the pUC19 vector harboring luciferase luxAB genes and the primers 5'-AGC<u>GGATCC</u>ATGAAATTTGG-3' (Seq. ID. No. 5: forward primer 1 for luxAB amplification) and 5'-CGTC<u>AAGCTT</u>ACGAGTGGTATTT-3' (Seq. ID. No. 6: reverse primer 1 for luxAB amplification). The underlined sequences are recognized by the restriction enzymes BamHI and HindIII, respectively. The purified PCR amplification product and pET28b-mOrange plasmid may be separately double-digested by BamHI and HindIII. The DNA fragments may be purified and may be ligated. The ligation mixture may then be added to *E. coli* BL21(DE3) competent cells for transformation. The cells may be plated on LB agar plates containing kanamycin and several colonies may be picked. Cell growth (in LB medium containing kanamycin) and plasmid extraction may be carried out. The desired plasmid, designated pET28b-OFG:α:β, so obtained harbored both the mOrange gene and the luciferase luxAB genes. The symbol ":" indicates that the two proteins on both sides of it are not fused. In this plasmid, a DNA fragment encoding a 20-residue peptide (MGSSHHHHHHSSGLVPRGSH)(Seq. Id. No. 28: 20-residue peptide) immediately precedes the start codon of the mOrange gene, which is followed sequentially by a non-coding sequence, luxA, another non-coding sequence, and luxB.

Vectors pET28b-mOrange-$L_5$-α:β and pET28b-mOrange-$L_{10}$-α:β.

The replacement of the non-coding region between mOrange and luciferase luxA with the sequence 5'-GGAGGAG-GAGGAACA-3' (Seq. ID. No. 7: nucleotide sequence for $L_5$) encoding the $L_5$ pentapeptide linker GlyGlyGlyGlyThr (Seq. ID. No. 1: 5-residue peptide linker abbreviated $L_5$) gives rise to the plasmid designated pET28b-mOrange-$L_5$-α:β. To this end, the pET28b-mOrange:α:β plasmid may be mutated using the QuikChange II kit and the primers 5'-GCATGGAC-GAGCTGTACAAGGGAGGAGGAGGAA-CAATGAAATTTGGAAACTTCCT-3' (Seq. ID. No. 8: forward primer for constructing pET28b-mOrange-$L_5$-α:β) and 5'-AGGAAGTTTCCAAATTTCATTGTTCCTC-CTCCTCCCTTGTACAGCTCGTCCATGC-3' (Seq. ID. No. 9: reverse primer for constructing pET28b-mOrange-$L_5$-α:β).

The same procedures described above for the preparation of pET28b-mOrange may be followed for the transformation of *E. coli* strain BL21(DE3) competent cells with the plasmid so obtained, cell growth, and isolation of the desired pET28b-mOrange-$L_5$-α:β plasmid. The expression of this plasmid produced the mOrange-$L_5$-α:β fusion enzyme in which the C terminus of mOrange may be fused (as indicated by "–") to the N terminus of the luciferase α subunit via the $L_5$ linker while the luciferase β remained non-covalently associated (as indicated by ":") with this modified α. For this mOrange-$L_5$-α:β designation, the individual protein components and the linker are also arranged (from left to right) in the same sequence as the locations of their encoding genes, with the most upstream gene corresponding to the first protein component in the designation (i.e. the mOrange gene and mOrange, respectively, in the present case). All other plasmids and their encoding fusion enzymes are designated following the same set of rules.

The plasmid pET28b-mOrange-$L_{10}$-α:β in which the non-coding region between mOrange and luciferase luxA is replaced by a sequence encoding the GlyGlyGlyGlyThrGlyGlyGlyGlyThr (Seq. ID. No. 2: 10-residue peptide linker abbreviated $L_{10}$) linker may be constructed the same way as that for pET28b-mOrange-$L_5$-α:β except by using the primers 5'-GGACGAGCTGTACAAGGGAGGAGGAG-GAACAGGAGGAGGAGGAACAA-3' (Seq. ID. No. 10: forward primer for constructing pET28b-mOrange-$L_{10}$-α:β) and 5'-TTGTTCCTCCTCCTCCTGTTCCTCCTC-CTCCCTTGTACAGCTCGTCC-3' (Seq. ID. No. 11: reverse primer for constructing pET28b-mOrange-$L_{10}$-α:β). The encoded fusion enzyme mOrange-$L_{10}$-α:β is similar to mOrange-$L_5$-α:β except that the C terminus of mOrange may be fused to the N terminus of α via the $L_{10}$ linker mentioned above.

Vectors pET21b-α:β and pET21b-α:β:mOrange.

The luciferase luxAB genes may be amplified by PCR using the pUC19 vector and primers 5'-CGTCCATATGAAATTTGGAAAC-3'(Seq. ID. No. 12: forward primer 2 for luxAB amplification) and 5'-CGTCAAGCTTACGAGTGGTATTT-3' (Seq. ID. No. 6: reverse primer 1 for luxAB amplification). The underlined sequences are recognized by the restriction enzymes NdeI and HindIII, respectively. The purified PCR amplification product and pET21b plasmid may be separately double-digested by NdeI and HindIII, and the digested products may be purified. DNA fragments so obtained (50 ng from plasmid template and 150 ng from PCR amplification product in 20 µL ligation solution) may be mixed with T4 ligase (400 U of in 1 µL), and incubated at 16° C. for 12 h for ligation. The ligated products may be used to transform the *E. coli* BL21(DE3)pLysS competent cells, and the treated cells may be plated on LB agar plates containing ampicillin and IPTG. As described above, several colonies may be selected and grown in LB medium containing ampicillin. Plasmids may be extracted from the harvested cells, and the desired pET21b-α:β vector may be isolated.

The mOrange gene may be amplified by PCR using pmOrange and primers: 5'-CGTCAAGCTTATGGTGAGCAA-3' (Seq. ID. No. 13: forward primer 2 for mOrange amplification) and 5'-TACGGCCGACTTGTACAGC-3' (Seq. ID. No. 14: reverse primer 2 for mOrange amplification). The underlined sequences are recognized by the restriction enzymes HindIII and EagI, respectively. The purified PCR amplification product and pET21b-α:β plasmid may be separately double-digested by HindIII and EagI, and ligations may be carried out using T4 DNA ligase. *E. coli* BL21(DE3)pLysS competent cells may be transformed with the ligated products, and may be plated on LB agar plates containing ampicillin and IPTG. Selected individual colonies may be grown in LB medium containing ampicillin, and plasmids may be extracted from harvested cells for the isolation of the desired pET21b-α:β:mOrange plasmid.

Vector pET21b-α:β-$L_5$-mOrange.

The non-coding region between luciferase luxB and mOrange in pET21b-α:β: mOrange may be mutated to the same DNA sequence encoding the $L_5$ linker as stated above by using the QuikChange lightning site-directed mutagenesis kit and the primers 5'-CGTCAAATACCACTCGGGAGGAG-GAGGAACAATGGTGAGCAAGGGCG-3' (Seq. ID. No. 15: forward primer for constructing pET21b-α:β-$L_5$-mOrange) and 5'-CGCCCTTGCTCACCATTGTTCCTCCTC-CTCCCGAGTGGTATTTGACG-3' (Seq. ID. No. 16: reverse primer for constructing pET21b-α:β-$L_5$-mOrange). Cell transformation, colony selection, cell growth, and plasmid extraction may be the same as that described for the preparation of pET28b-mOrange-$L_5$-α:β except that ampicillin may be used replacing kanamycin in both the LB agar and liquid media. The desired pET21b-α:β-$L_5$-mOrange plasmid so obtained encoded the fusion enzyme α:β-$L_5$-mOrange in which the C terminus of luciferase β may be fused with the N terminus of mOrange via the $L_5$ linker and this modified β may be non-covalently associated with the luciferase α.

Vectors pET21b-β, pET21b-β:α, and pET21b-β:α:mOrange.

The luciferase luxB gene may be amplified by PCR using the pUC19 vector and the primers: 5'-GACCATATGAAATTTGGATTATTCTTC-3' (Seq. ID. No. 17: forward primer for luxB amplification) and 5'-GATGGATCCTTACGAGTGGTATTT-3' (Seq. ID. No. 18: reverse primer for luxB amplification). The underlined sequences are recognized by restriction enzymes NdeI and BamHI, respectively. The purified PCR amplification product and pET21b plasmid may be independently double-digested by NdeI and BamHI, and ligated using T4 DNA ligase. The sample so obtained may be used to transform *E. coli* BL21 (DE3)pLysS competent cells. The cells may then be plated on LB agar plates and several single colonies may be individually grown in LB medium, both containing ampicillin. Plasmids may be extracted and the desired pET21b-β plasmid may be isolated. The luciferase luxA may also be amplified by PCR using with the pUC19 vector and primers 5'-CA GAGCTCATGAAATTTGGAAAC-3' (Seq. ID. No. 19: forward primer for luxA amplification) and 5'-CGTC AAGCTTACTGTTTTTCTTTGA-3' (Seq. ID. No. 20: reverse primer for luxA or luxBA amplification). The underlined sequences are recognized by the restriction enzymes SacI and HindIII, respectively. The purified PCR amplification product and pET21b-β may be independently double-digested by SacI and HindIII, and ligated using T4 DNA ligase. The same procedures described for pET21b-β may be then followed for the isolation of a plasmid which contained, sequentially, the luciferase luxB, a non-coding sequence, and luxA. However, the non-coding sequence had no ribosome binding site (rbs) upstream of the luciferase luxA. The rbs is needed for the translation of luciferase α. Therefore, the non-coding region may be replaced by 5'-AAG-GAGAGAGAC-3' for the insertion of the rbs site by mutation using the primers 5'-AACATCGTCAAATACCACTCG-TAAAAGGAGAGAGACATGAAATTTG-GAAACTTCCTTCTC-3' (Seq. ID. No. 21: forward primer for constructing pET21b-α:β) and 5'-GAGAAG-GAAGTTTCCAAATTTCATGTCTCTCTC-CTTTTACGAGTGGTATTTGACGATGTT-3' (Seq. ID. No. 22: reverse primer for constructing pET21b-β:α). Following the same procedures as stated above, a plasmid designated pET21b-β:α may be obtained the expression of which produced active native luciferase.

The mOrange may be amplified by PCR using the mOrange plasmid and the primers 5'-CGTC AAGCTTATGGTGAGCAA-3' (Seq. ID. No. 13: forward primer 2 for mOrange amplification) and 5'-TA CGGCCGACTTGTACAGC-3' (Seq. ID. No. 14: reverse primer 2 for mOrange amplification). The underlined sequences are recognized by the restriction enzymes HindIII and EagI, respectively. The purified PCR amplification product and the pET21b-β:α plasmid may be independently double-digested by HindIII and EagI, and may be ligated using T4 DNA ligase. Same as described above, the desired plasmid pET21b-β:α: mOrange may be isolated which encodes the functionally active luciferase and mOrange but none of these protein components will be fused.

Vector pET21b-β:α-L$_5$-mOrange.

The replacement of the non-coding region between the luciferase luxA and mOrange with the same sequence encoding the L$_5$ linker may be conducted using the pET28b-mOrange:α:β plasmid and the primers 5'-ATATCTCAAA-GAAAAACAGGGAGGAGGAGGAACAATGGTGAGCA-AGGGCGAGG-3' (Seq. ID. No. 23: forward primer for constructing pET21b-β:α-L$_5$-mOrange) and 5'-CCTCGCCCT-TGCTCACCATTGTTCCTCCTCCTCCCT-GTTTTTCTTTGAGATAT-3' (Seq. ID. No. 24: reverse primer for constructing pET21b-β:α-L$_5$-mOrange).

The non-coding region between the mOrange and luciferase α may be replaced by 5'-GGAGGAGGAG-GAACA-3'. The same procedures as stated for pET21b-β may be followed, except that IPTG may also be included in the LB agar medium, for the isolation of the plasmid pET21b-β:α-L$_5$-mOrange. The expression of this plasmid gives rise to the production of the fusion enzyme β:α-L$_5$-mOrange, in which the C terminus of α is fused with the N terminus of mOrange via the L$_5$ linker and the β is non-covalently associated with this modified α.

Vectors pET28b-mOrange:β:α and pET28b-mOrange-L$_5$-β:α.

The pET21b-β:α may be used for PCR along with primers 5'-TACGGATCCATGAAATTTGGATT-3' (Seq. ID. No. 25: forward primer for luxBA amplification) and 5'-CGTC AAGCTTACTGTTTTTCTTTGA-3' (Seq. ID. No. 20: reverse primer for luxA or luxBA amplification). The underlined sequences are recognized by the restriction enzymes BamHI and HindIII, respectively. The purified PCR amplification product and pET28b-mOrange may be independently double-digested by BamHI and HindIII, and may be ligated using T4 DNA ligase. The sample may then be used to transform *E. coli* BL21(DE3)pLysS competent cells. The same procedures as stated for pET28b-mOrange may be then followed for the isolation of the plasmid pET28b-mOrange:β:α. The replacement of the non-coding region between mOrange and luciferase luxB with the same sequence for the L$_5$ linker may be conducted by mutation of pET28b-mOrange:β:α. using the primers 5'-GGCATGGACGAGCTGTACAAGG-GAGGAGGAGGAACAATGAAATTTGGAT-TATTCTTCC-3' (Seq. ID. No. 26: forward primer for constructing pET28b-mOrange-L$_5$-β:α) and 5'-GGAA-GAATAATCCAAATTTCATTGTTCCTCCTCCTCCCT-TGTACAGCTCGTCCATGCC-3' (Seq. ID. No. 27: reverse primer for constructing pET28b-mOrange-L$_5$-β:α). The plasmid solution may then be used to transform *E. coli* BL21 (DE3) competent cells.

The transformed cells may be subsequently subjected to the same treatments as described for pET28b-mOrange:β:α cells for the isolation of the vector pET28b-mOrange-L$_5$-β:α. For the fusion enzyme mOrange-L$_5$-β:α encoded by this plasmid, the L$_5$ linker is fused to the N terminus of luciferase β while α is non-covalently associated with this modified β.

Protein Purification.

*V. harveyi* luciferase and FRP may be purified as previously describe. For the expression and isolation of luciferase-mOrange fusion enzymes, *E. coli* BL21(DE3) or *E. coli* BL21 (DE3)pLysS cells carrying the plasmids for luciferase-mOrange fusion enzymes or mOrange may be grown in 1 L Luria-Bertani with 50 mg/L kanamycin (for plasmids originated from pET28b) or 50 mg/L ampicillin (for plasmids originated from pET21b) at 37° C. and may be shaken at 250 rpm in a C25KC Incubator Shaker (New Brunswick Scientific) until OD$_{600\ nm}$ reaches about 1.0. IPTG may be added into the cell culture at 1 mM. The cell culture may be incubated at 28° C. at 250 rpm for another 20 h. Cells may be harvested by centrifugation at 7000 rpm for 1 h using a Beckman Coutler J2-HS centrifuge. The cell pellet so obtained may be suspended in 35 mL ice-cooled binding buffer (i.e. the standard buffer of 50 mM Pi, pH 7.0, supplemented with 0.5 M NaCl, 0.5 mM DTT and 20 mM imidazole) and sonicated on ice for 7.5 min by using a Fisher Scientific sonic dismembrator model 500. The cell lysate may be centrifuged at 14,000 g for 30 min, and the supernatant may be collected and filtered through a 0.2-μm PES filter. The filtrate may be loaded on a 5-mL HisTrap HP column equilibrated with the binding buffer. The column may be eluted first with the same binding buffer until absorbance at 280 nm reaches near zero, and then with an elution buffer (standard buffer containing 0.5 M NaCl, 0.5 mM DTT and 500 mM imidazole). Fractions containing the desired fusion protein may be identified by A$_{280}$ and the fluorescent-protein color for collection. The pooled fractions may be applied to a HiPrep 26/10 desalting column, and recovered in the standard buffer containing 0.5 mM DTT. The sample may be then loaded on a Mono Q 5/50 GL column pre-equilibrated and then eluted with the same standard buffer containing 0.5 mM DTT until the absorbance at 280 nm reaches near zero. Subsequently, a (15 column volume) gradient of 0-0.5 M NaCl in the standard buffer containing 0.5 mM DTT may be applied. Fractions containing the desired fusion enzymes may be collected, pooled, and loaded on a HiPrep 26/10 desalting column for recovering the fusion enzymes in the standard buffer containing 0.5 mM DTT. Protein concentrations may be determined by using the DC protein assay kit from Bio-Rad and chicken egg white albumin as a standard.

Enzyme Assays.

Activities of native luciferase and all luciferase-mOrange fusion enzymes may be determined at room temperature by the dithionite assay or by the photoreduction assay, both in the standard buffer without (for the former) or with 20 mM EDTA (for the latter assay). In both assays, luciferase catalyzes a non-turnover single cycle reaction, for which the bioluminescence peak intensity, the total quantum output and, for the dithionite assay, the light decay rate may be measured. The arbitrary light intensities recorded may be converted to quantum (q) per second by calibration with a liquid light standard (19). For some bioluminescence measurements, a yellow cut-off filter (10BPF10-480 7G311; 480±2 nm bandpass and <1% transmission at <460 nm) and an amber cut-off filter (10BPF10-570 7C299; 570±2 nm bandpass and <1% transmission at <532 nm) from Newport Company may also be used.

Measurement of Bioluminescence Spectra.

A Varian Cary 50 spectrometer and a Varian Cary Eclipse fluorometer may be used for the measurements of absorption spectra and fluorescence/bioluminescence spectra, respectively. For the bioluminescence emission spectral measurements, an FRP-coupled bioluminescence reaction may be initiated by rapidly mixing FRP with NADPH, FMN, decanal and luciferase (or fusion enzymes) in a fluorescence cuvette. The bioluminescence emission spectrum may be measured when the bioluminescence emission reaches a steady level.

Natural extensions of the present disclosure may be improvements in the energy transfer efficiencies observed with mOrange-$L_5$-α:β and mOrange-$L_{10}$-α:β by using other fluorescent proteins or linkers of choice following the same approach as described above. Further, similar approaches may be used to generate various fluorescent protein- or fluorescent chromophore-attached luciferases as multiple color emitters. For exemplary purposes, where a fluorescent protein is used as the energy acceptor, the fusion enzyme may be used as sensor for both in vitro and in vivo systems. Suitable organic fluorophores may also be used as the energy acceptor after chemical linking to luciferase as long as their absorption overlaps with the normal bacterial bioluminescence, and their fluorescence emission is in a wavelength range higher than the luciferase bioluminescence. By using organic fluorophores, bacterial luciferase may also be converted to multicolor sensors. However, the fluorophore-attached luciferase is best suited for in vitro systems.

The foregoing description of the preferred embodiments is provided to enable any person skilled in the art to make or use the claimed subject matter. Various modifications to these embodiments will be readily apparent to those skilled in the art, and the generic principles defined herein may be applied to other embodiments without the use of the innovative faculty. Thus, the claimed subject matter is not intended to be limited to the embodiments shown herein but is to be accorded the widest scope consistent with the principles and novel features disclosed herein.

The detailed description set forth above in connection with the appended drawings is intended as a description of exemplary embodiments in which the presently disclosed compositions and methods can be practiced. The term "exemplary" used throughout this description means "serving as an example, instance, or illustration," and should not necessarily be construed as preferred or advantageous over other embodiments.

Further, although exemplary embodiments disclosed above implement the elements of the disclosed subject matter have been provided, one skilled in the art, using this disclosure, could develop additional compositions, methods, hardware, and/or software to practice the disclosed subject matter and each is intended to be included herein.

In addition to the above described embodiments, those skilled in the art will appreciate that this disclosure has application in a variety of arts and situations and this disclosure is intended to include the same.

What is claimed is:

1. A luminescent sensor system comprising:
a fusion molecule complex, wherein said fusion molecule complex is comprised of an energy donor molecule attached to an energy acceptor molecule, wherein said energy donor molecule is comprised of a bacterial luciferase, wherein said energy acceptor molecule is comprised of a fluorescent protein having an absorption spectrum that overlaps with an emission of normal bacterial luciferase bioluminescence and a fluorescence emission spectrum that is higher in wavelength range than the normal bacterial luciferase bioluminescence, and further wherein after said energy donor molecule is attached to said energy acceptor molecule, said energy acceptor molecule produces a different luminescence, and further wherein said energy donor maintains wild-type luminescent activity; and
a plurality of substrates comprising $FMNH_2$, wherein said plurality of substrates interact with said fusion molecule complex for producing luminescence.

2. The luminescent sensor system of claim 1, wherein at least one of said plurality of substrates supports a bioluminescent reaction catalyzed by bacterial luciferase.

3. The luminescent sensor system of claim 1, further wherein said fluorescent protein being fluorescent protein mOrange.

4. The luminescent sensor system of claim 1, wherein said energy acceptor molecule is comprised of a fluorescence acceptor chromophore.

5. The luminescent sensor system of claim 1, wherein said energy acceptor molecule is comprised of an organic fluorophore.

6. The luminescent sensor system of claim 5, further comprised of a plurality of multi-color sensors.

7. The luminescent sensor system of claim 1, further wherein said bacterial luciferase is attached to a fluorescent protein by a covalent linkage.

8. The luminescent sensor system of claim 7, further wherein said energy transfer between said bacterial luciferase and said fluorescent protein causes a shift in its emission spectrum.

9. The luminescent sensor system of claim 7, further wherein said fluorescent protein is attached to an alpha-subunit of said bacterial luciferase.

10. The luminescent sensor system of claim 9, further wherein said fluorescent protein is attached to an N-terminus of said alpha-subunit of said bacterial luciferase.

11. The luminescent sensor system of claim 10, further wherein said covalent linkage is comprised of a short peptide linker.

\* \* \* \* \*